United States Patent [19]
Tabata et al.

[11] Patent Number: 5,602,645
[45] Date of Patent: Feb. 11, 1997

[54] PATTERN EVALUATION APPARATUS AND A METHOD OF PATTERN EVALUATION

[75] Inventors: Mitsuo Tabata, Yokohama; Toru Tojo, Kanagawa-ken; Kiminobu Akeno, Yokohama; Toshiyuki Watanabe, Yokohama; Tomohide Watanabe, Yokohama; Eiji Yamanaka, Yokohama; Chikara Itoh, Matsudo; Makoto Taya, Tokyo, all of Japan

[73] Assignees: Kabushiki Kaisha Toshiba, Kawasaki; Kabushiki Kaisha Topcon, Tokyo, both of Japan

[21] Appl. No.: 527,633

[22] Filed: Sep. 13, 1995

[30]   Foreign Application Priority Data

Sep. 16, 1994   [JP]   Japan ................... 6-221871

[51] Int. Cl.⁶ .................................................. G01B 11/00
[52] U.S. Cl. ........................ 356/394; 356/390; 356/368; 356/237
[58] Field of Search ................................ 356/394, 237, 356/429, 239, 388, 390, 30

[56]   References Cited

U.S. PATENT DOCUMENTS 2,898,801   8/1959   Rockafellow .................... 356/394
4,165,939   8/1979   Woodrow et al. ................ 356/237
4,244,652   1/1981   Berger et al. ................... 356/394
4,377,340   3/1983   Green et al. .................... 356/237
5,400,135   3/1995   Maeda ............................ 356/237

FOREIGN PATENT DOCUMENTS

4-100045   4/1992   Japan .

Primary Examiner—Frank Gonzalez
Assistant Examiner—Reginald A. Ratliff
Attorney, Agent, or Firm—Oblon, Spivak, McClelland, Maier & Neustadt, P.C.

[57]   ABSTRACT

The present invention provides a pattern evaluating device including light irradiating means for irradiating the rays of light from a light source upon an object, an objective lens through which the light having penetrated through the object passes, an aperture member stopping the diameter of a light beam which has passed the objective lens, a photo receiving element receiving the light beam which has had the diameter stopped by the aperture member, and judging means for evaluating the pattern, following the information of the light received by the photo receiving element and which corresponds to the pattern, wherein the aperture member is capable of changing the numerical aperture, depending whether or not the sample is provided with a pericle.

13 Claims, 7 Drawing Sheets

PATTERN EVALUATION APPARATUS AND A METHOD OF PATTERN EVALUATION

BACKGROUND OF THE INVENTION

1. Field of the Invention

The present invention relates to a pattern evaluation apparatus and a method of pattern evaluation, and particularly to such an apparatus and a method which are applied, respectively, to inspect the defects of those patterns formed each on a photo mask or the like for use in the manufacture of semiconductor devices.

2. Description of the Related Art

The defects of photo masks used in the production of semiconductor devices with the photo lithographic technology applied are counted as one of major causes of decreasing the yield in the manufacture of large scale integrated circuits (LSI). Therefore, the development of devices to inspect such defects has thus far been actively carried out, with some then brought into practical services.

Conventional photo mask defect inspecting apparatus are roughly divided into two categories—one which follows a method wherein two chips having the same pattern formed thereon each are first inspected by separate detecting means, and the differences which the respective patterns exhibit in reference to each other are subsequently compared with one another, using proper defect detecting means; and another which is based on a method wherein each chip with a pattern provided thereon is observed, using detecting means, followed by comparing actual pattern data with pattern design data through appropriate defect detecting means to find out a defect. Since the former apparatus observes two chips which have the same pattern formed thereon each, should there exist an identical defect in each of these patterns, the device will fail to detect a defect portion where the defect is present, disclosing its shortcoming. However, said apparatus has a merit that a design data processing circuit is unnecessary, whereby the apparatus constitution may be simplified. Meanwhile, the latter apparatus is of a constitution wherein the inspection is effected with design data applied as a data base, thus showing on one hand a merit that defect detection is perfect and on the other hand a demerit that there takes place structural complexity. These defect inspecting apparatus undertake the detection of extra minute defects, thus having so far been experiencing the improvements not only for better resolutions of the optical systems but also of the comparison algorithm, the method of measured signal processing, and so forth.

Figures 1, 2, 3A, 3B:
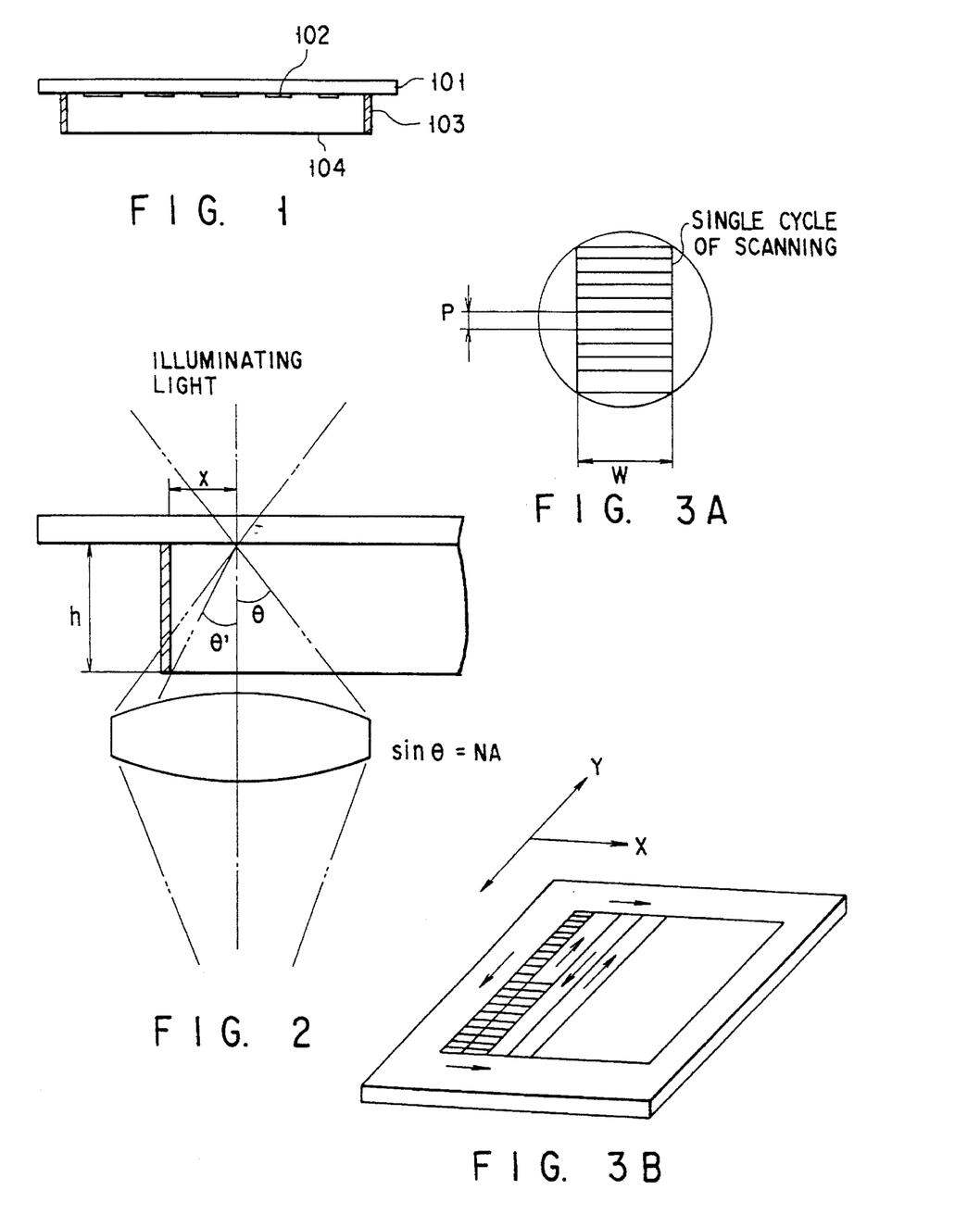
FIG. 1 is a view depicting a pericle fitted to one photo mask.
FIG. 2 is a view illustrating a difference which the inspection area makes, depending on whether or not there is provided a pericle.
FIGS. 3A and 3B present a pattern evaluating method respectively.

On the other hand, of late, to avoid the trouble that microscopic dust particles will deposit on the surface of each sample, a glass substrate 101 which has once had a perfect pattern 102 provided thereon is brought into use with a pericle frame 103 stuck (bonded) thereto as shown in FIG. 1 with a several μm thick thin film 104 called a pericle affixed thereto. Thus, it is required that the photo mask defect inspecting apparatus undertake pre-pericle sticking inspection and post-pericle sticking inspection for final check.

Generally with the optical system-mounted devices such as photo mask defect inspecting apparatus, it is known that increasing the numerical aperture (NA) of an objective lens is serviceable to improve the characteristic of resolving an image of each pattern to be observed. Recent photo mask defect inspecting devices are required capable of detecting a defect of less than 0.3 μm, wherein the optical systems which have so far been brought into service with NA=approximately 0.5 to 0.6 selected, are needed of late to go into use with NA=approximately 0.7 to 0.8. These devices raise no problem over the inspection of pericle free photo masks. However, as the numerical aperture (NA) of an objective lens grows as shown in FIG. 2, the photo mask defect inspecting apparatus have their serviceability limited to the inspection areas narrower than ever. Namely, they are limited to inspect only the area far remote from the pericle frame. This is because, as illustrated in FIG. 2, the pericle frame interrupts the rays of light, with the light beam getting asymmetric, whereby there occurs a change of the luminous energy. Since the size of a pericle frame, the dimensions of a pattern forming area, etc. depend, to a certain degree, on device design particulars and what is the peripheral apparatus involved (a stepper, etc. for example), it is desired that the defect inspecting apparatus be capable of inspecting pericle fitted photo masks over their wide possible areas with the high accuracy of detection kept unchanged.

As a means to solve such problems, a method is available wherein the problems are settled with the NA of an optical system on the side of observation lessened. But the effect in the fall of detecting accuracy stemming from provision of a smaller NA is not nullified.

SUMMARY OF THE INVENTION

The present invention has been achieved with the above well reflected, and aims at providing a device and a method capable of undertaking high-precision pattern evaluation over a wider area of each pattern, nevertheless a pericle fitted photo mask is used.

A first object of the present invention is to provide a pattern evaluating device which comprises light irradiating means for irradiating the rays of light from a light source upon an object a pattern, an objective lens through which the light having penetrated through the object passes, an aperture member stopping the diameter of a light beam which has penetrated through the objective lens, a photo receiving element receiving the light beam which has had the diameter stopped by the aperture member, and judging means to evaluate the pattern, following the information of the light received by the photo receiving element and which corresponds to the pattern, wherein the aperture member is capable of changing the numerical aperture according to whether or not there is provided a pericle.

A second object of the present invention is to provide a pattern evaluating device which comprises light irradiating means for irradiating the rays of light from a light source upon an object with a pattern, an objective lens through which the light having penetrated through the object passes, an aperture member stopping the diameter of a light beam which has passed through the objective lens, a photo receiving element receiving the light beam which has had the diameter stopped by the aperture member, and judging means to evaluate the pattern, following the information of the light received by the photo receiving element and which corresponds to the pattern, wherein the object is provided with a pericle, and the judging means evaluates the pattern, according to the information obtained via arithmetic processing of the information corresponding to the pattern, at the time of inspecting the neighborhood of the pericle's edge portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

The first embodiment of the present invention is characterized by the changeability of a numerical aperture with an aperture member applied, depending on whether or not a sample (object) is provided with a pericle.

As first means of the first embodiment, a large NA objective lens is used for normal inspection, wherein for inspecting a pericle fitted sample, the objective lens is not replaced with another but the lens has its aperture NA on a sample side changed. In this arrangement, it is allowed that the large NA objective lens is used as before with NA unchanged for inspecting a pericle free sample, whereby defect detection with high accuracy is feasible while in case where a pericle fitted sample is inspected, the objective lens is used with its numerical aperture NA slightly lessened, whereby the inspection area may be expanded larger than before.

Further, as second means of the first embodiment, there is provided an aperture member setting the NA of an optical system with its aperture profile selected in an approximate rectangle, wherein the rectangular profile of a pericle frame provides effective serviceability, whereby defect detection is practicable with the accuracy higher than the case where the aperture member with a circular aperture profile is used.

It is noted here that as respective methods for changing the numerical aperture according to whether or not the sample is provided with a pericle, a method wherein a large NA objective lens is used for normal inspection, but for inspecting a pericle-provided sample, the objective lens is not replaced with another, with the NA thereof on a sample side varied, and a method wherein an aperture member for setting the NA of an optical system has its aperture selected in an approximate rectangle are included.

In the first embodiment of the present invention, it is preferred that means for adjusting the luminous energy be further provided so that the luminous energy of light incident upon a photo receiving element may be approximately constant along with a change of the numerical aperture. Provision of this means results in achieving higher serviceability meeting the demands for various evaluations not requiring gain readjustment, etc. to a large extent of a photo receiving element circuit.

Further, the pattern evaluating method to which the first embodiment of the present invention relates is characterized in that a process of converging, by light focusing means, the rays of light from a light source upon a sample carrying a pattern, a process of stopping, by an aperture member, the diameter of a light beam which penetrated through said sample, and a process of pattern evaluation wherein a photo receiving element receives the light beam which has had its diameter focused and said pattern is inspected for evaluation, following the information of the light received thereby and which corresponds to said pattern are included, and the numerical aperture is changed by said aperture member according to whether or not said sample is provided with a pericle.

The following are the configurational particulars characterizing the first embodiment of the present invention:

(1-a): The aperture member setting the numerical aperture of an objective lens on the side of a sample must have its aperture profile selected in an approximate rectangle which herein refers to an approximate square, an oblong, an approximate oval, an ellipse, etc.

(1-b): The aperture member must be incorporated in the device concerned, regardless of whether or not there is provided a pericle.

(1-c): The aperture member or luminous energy adjusting means must be capable of being driven through computer control according to the information which the operator inputs concerning whether or not there is provided a pericle, or the signal of detection as to if the pericle is provided.

(1-d): The straight line portions within the aperture of the aperture member must be parallel respectively to the straight line portions of a pericle frame.

(1-e): The NA, on the sample side of the objective lens, which is stopped by the aperture member must be somewhat larger than theoretical NA (=sin (tan$^{-1}$ (x/h))) which is calculated with the pericle height assumed as h, and the distance between from the pericle frame to the portion where defect inspection is impracticable likewise assumed as x.

The second embodiment of the present invention is characterized in that each sample is provided with a pericle, and pattern evaluation is carried out, following the information through with arithmetic processing and which corresponds to a pattern involved, when pattern inspection is effected near the pericle edge portion.

This arrangement allows that the same large NA objective lens is used with NA unchanged, regardless of whether or not samples are provided each with a pericle, whereby defect detection may be effected with high sensitivity in evaluating pericle fitted patterns. In conventionality with NA being approximately 0.8, the area which is left uninspected, extends by a width of approximately 10 mm from the pericle frame while with the present invention, the area left uninspected is within a width of approximately 1 mm, with practicability to greatly expand the inspection area made available.

In the second embodiment of the present invention, it is preferred that arithmetic processing be a processing to vary the output gain or offset which the photo receiving element exhibits, in reference to a standard value, in response to the reception of the light corresponding to a pattern, and further that the processing to alter this gain or the offset be effected based on the position of inspecting. It is noted here that the standard value of the light corresponding to a pattern includes standard image data, etc.—prepared from the design data of a pattern—with which measured image data is compared, let alone the data output from the photo receiving element.

Further, the method of pattern evaluation to which the second embodiment of the present invention relates is characterized in that a process of converging, by light focusing means the rays of light from a light source upon a sample having a pericle and carrying a pattern, and a process of evaluating said pattern according to the information of the light received by the photo receiving element upon passage through said sample and subsequently received by the photo receiving element and which corresponds to said pattern, are included, and the evaluation of said pattern is conducted, following the information obtained via arithmetic processing of the information of the light corresponding to said pattern.

The following are the configurational particulars characterizing the second embodiment of the present invention:

(2-a): The output gain or offset in reference to the input of measured image data or standard image data must be changed in the unit of an inspection width.

(2-b): There must further be provided memory means to store the falling rates of the luminous energy of light incident upon in the inspection near the pericle frame.

(2-c): One portion undergoing some effect from a fall of the luminous energy of the projected upon a sensor in the inspection near the pericle frame, and another portion relatively remote from the pericle frame and where there does not take place a fall of luminous energy must separated for separate inspection.

(2-d): Serial inspection must be effected with the output gain or offset in reference to the input of measured image data or standard image data changed regardless of the portion suffering some effect from a fall of the luminous energy of light incident upon a sensor in the inspection near the pericle frame and the other portion relatively remote from the pericle frame and where there does not occur a fall of luminous energy.

(2-e): There must further be provided memory means to not only judge whether or not the sample has a pericle but also subsequently store the consequence of judgment.

(2-f): The modified values respectively of the output gain or offset in reference to input measured image data or input standard image data must be approximately uniform in reference to the pixcel gain of the sensor or the output gain of an offset regulator or standard image data. Further for higher accuracy, the gain or offset may be compensated for with each pixcel, using the method of interpolation.

(2-g): Means to detect the position of the pericle frame fitted to a photo mask must further be provided.

(2-h): The means to measure the position of the pericle frame must be such as decides the pericle frame position from the luminous energy change rate which is given by a sensor output when a slide table is moved respectively in each of x and y directions.

(2-i): The means to detect the position of the pericle frame must be such as decides the pericle frame position from the change of an auto focusing sensor output at the time the slide table is moved in each of x and y directions.

It is noted in the second embodiment of the present invention that the position of a pericle fitted to the sample is detected, and subsequently, the data of a detected position is fed back in the inspection near the pericle frame, with the position data thereby compensated for sufficiently, and accurately, whereby pattern evaluation with higher accuracy is made feasible.

In each of the first and second embodiments of the present invention, either of the methods is serviceable for pattern evaluation, in one of which two samples having the same pattern each are observed separately by respective detector means, followed by comparing the difference which these samples have shown in reference to one another, and in the other of which each sample with a pattern is observed by detector means, and detected pattern data is compared with design pattern data for defect detection.

The present invention is applicable for inspecting wafer patterns, in addition to photo mask pattern defect detection.

The embodiments of the present invention are described in detail with reference to the drawings.

Embodiment 1

As regards this embodiment, a pattern evaluating device for detecting photo mask pattern defects, using design data, is described hereunder. Such photo mask pattern evaluation is disclosed in "Denshi Zairyo (Electronics Materials)", September 1983 Edition, Page 47 covering a high-precision full-automatic reticle inspection device for VLSIs.

Photo mask pattern evaluation in this embodiment is effected by magnifying a photo mask pattern using an optical system, etc. and then, as shown in FIG. 3A serially measuring a narrow paper strip arrayal in the arrow direction specified in FIG. 3B, each strip measuring a width (W) of approximately 500 μm (practically, a table is moved continuously in each of X and Y directions).

Figure 4:
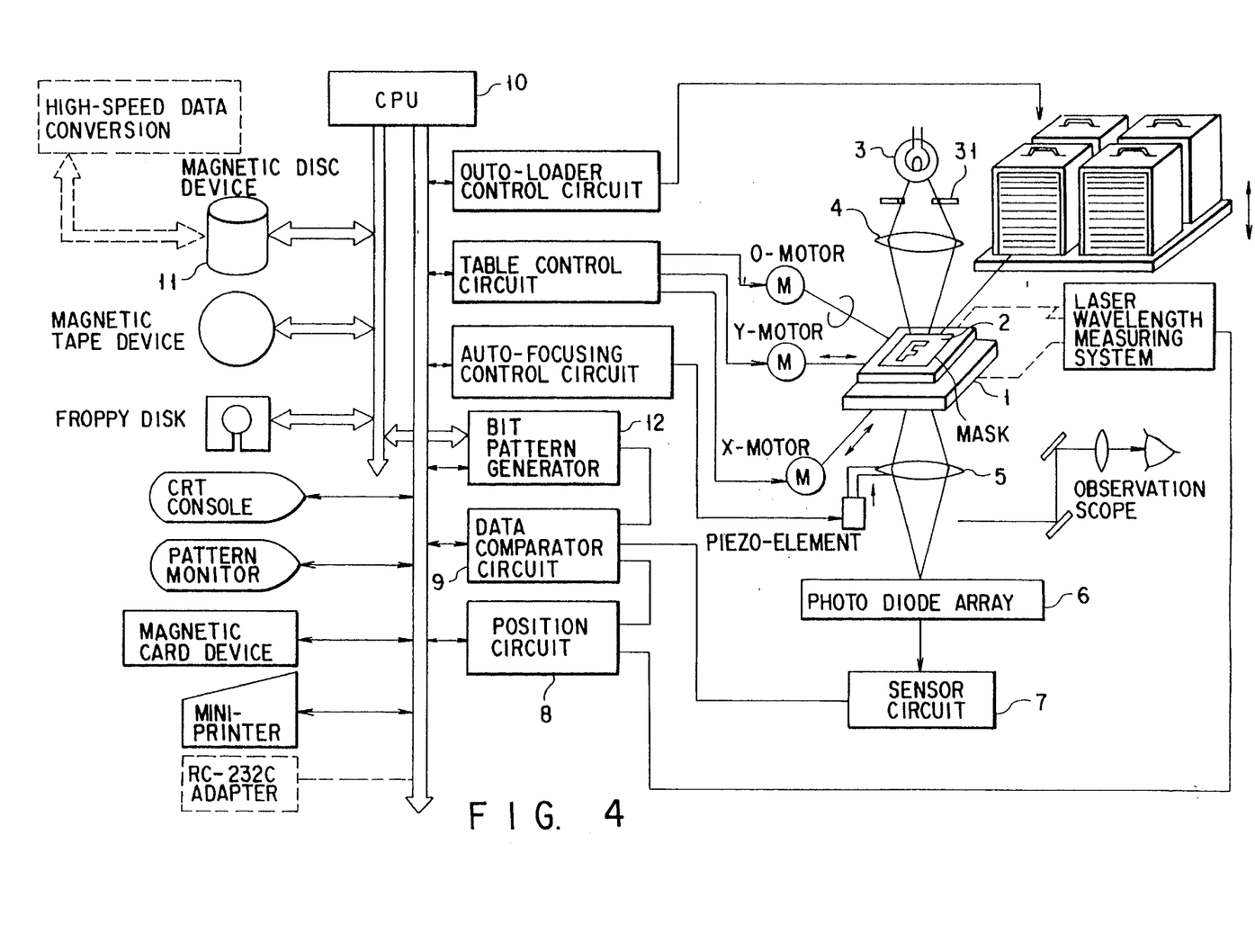
FIG. 4 is a configuration illustration chart showing one example of a pattern evaluating device.

Next, referring to FIG. 4, the method of photo mask pattern evaluation is described hereunder. First, a photo mask 2 is set on a table 1 movable in each of X, Y and θ directions, and the rays of light from a proper light source 3 are projected on a pattern upon being converged by a condenser lens 4. The light which has passed through the photo mask 2, goes through an objective lens 5, getting focused and forming a pattern image upon a photo diode array 6, with subsequent A/D conversion being effected by a sensor circuit 7. Measured pattern data is transferred together with the position data from a position circuit 8 to a comparator circuit 9. Meanwhile, pattern design data is transferred via a magnetic disc device 11 and a control computer 10 to a bit pattern generator 12 wherein figure data is converted into binary-coded bit pattern data which is then transferred to the comparator circuit 9. In the comparator circuit 9, the binary-coded bit pattern data is given a filtration process, for the conversion into multi-digital data. This is because the measured pattern data is affected not only by the resolution characteristic of the objective lens 5 but also by the aperture effect of the photo diode array 6, with said measured pattern data getting forced as if to remain under the action of a filter, and to cope with this situation, the pattern design data is likewise given a filtration process whereby said pattern design data may match the measured data. These two data are compared, following an adequate algorithm, wherein a part of the measured pattern data, which was found failing to agree with its counterpart of the pattern design data is judged as a defect.

In such a method of pattern evaluation, a large NA optical system (NA=0.8, etc. for example) is employed to improve the resolution characteristic of the objective lens 5, whereby the detection of extra minute defects is rendered easy. Of late, however, for the final inspection of a pericle fitted photo mask as shown in FIG. 1, namely for the final inspection to confirm whether or not the fitting of a pericle has left behind a flaw or if there has taken place the deposition of dust particles, said device has come to be used. Therefore, as described with reference to FIG. 1, use of a large NA optical system results in causing the pericle frame to interrupt the beam of light, with the inspection area narrowing thereby and the trouble of failing to inspect the pattern region peripheral portion brought out. Further, as referred to above, a pericle fitted photo mask is used for the final inspection to find a flaw and the deposition of dust particles, and the photo mask is presently allowed of some fall in pattern defect detection sensitivity. Taking notice of such a fact, the co-inventors of the present invention will provide a pattern evaluating device wherein NA is variable at the time when pattern inspection is progressing, and pattern evaluation with high accuracy is practicable.

Figures 5, 6A, 6B, 6C:
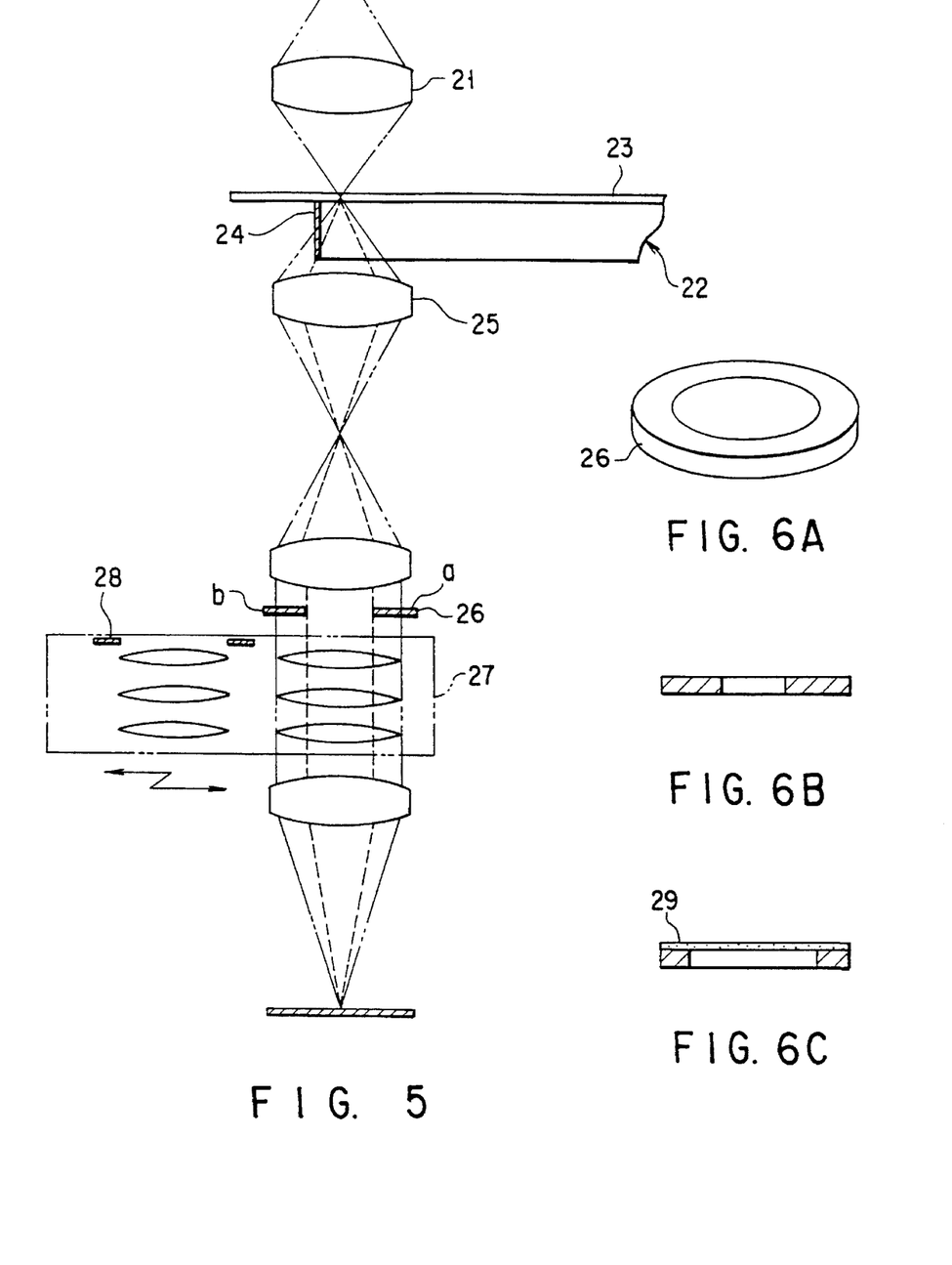
FIG. 5 is a rough sketch showing one embodiment of the pattern evaluating device according to the present invention.
FIGS. 6A through 6C are respective views, each showing a profile of the NA aperture-stop for use with the pattern evaluating device of the present invention.

FIG. 5 is a conceptual diagram showing one embodiment of a pattern evaluating device according to the present invention. The beam of light with the rays converged by a condenser lens 21 goes through an objective lens 25, aperture 26 of an aperture member and further through a group of lens arranged behind them, becoming a parallel ray light. Generally, at this portion, a magnification changing system 27 is provided to adjust the magnification of the optical system, forming a configuration wherein the group of lenses is allowed of replacement with another as occasion demands. Subsequently, the light is converged upon a photo diode array, with an image of the photo mask pattern is focused upon a sensor. Presented in FIG. 5 is the beam of light passing through the maximum NA of the objective lens.

In case where a pericle 22 is fitted to the photo mask, the beam of light is interrupted as shown in FIG. 5. Interruption of the light beam results in changing the luminous energy of the photo mask pattern image on the sensor, with the sensitivity of defect detection at the portion where the interruption of light is under way, getting declined. Therefore, when the photo mask is confirmed of being fitted with the pericle 22, NA is adjusted, using the aperture 26 installed at the portion where the parallel ray light is prepared. This adjustment is serviceable not only to free the light from undergoing the interruption by a pericle frame 24 but also to enable the inspection up to the neighborhood of the pericle frame 24. To automatically confirm that the photo mask is fitted with the pericle 22, the information of given pericle fitted photo mask is input in advance to a control system or a pericle confirmation sensor is installed.

Here, with reference to FIGS. 6A through 6C, the aperture 26 is described. When the diameter of the aperture 26 in FIG. 6A is changed, the luminous energy of the light projected upon a sensor varies. Thus with the aperture-stop NA to a small size, there is thereby formed an opening allowing unrestricted passage of light as shown in FIG. 6B. Further, in case with the aperture-stop NA to the maximum diameter, provision of an ND filter 29 on a ring proper as shown in FIG. 6C enables to make constant the luminous energy of the light projected upon the sensor. With the ND filter 29 installed such as the above, it becomes possible to relieve the sensor circuit of gain shearing, whereby a circuit with a great S/N ratio may be designed. The ND filter 29 for luminous energy adjustment may be installed at any position within an illuminating optical system, and particularly, incurs no structural limitation as shown in FIG. 6C.

This embodiment allows use of a known device such as a motor, etc. as drive means which drives the aperture 26 shown in FIG. 5 for insertion into a given position. This drive means serves not only to set the aperture 26 at a given position within the optical system when a pericle is provided, but also remove the aperture 26 from within the optical system when no pericle is provided. Further, the inspection may be effected by integrally switching, depending on whether or not there is provided a pericle, to another magnification changing system 28 prepared in advance, to which an aperture is fixed, Further, as is understood from FIG. 5, it is allowed that the aperture 26 is split into respective parts, wherein when the pericle frame 24 is positioned on the left in FIG. 5, the a-side aperture part is inserted into place while in case where the pericle frame 24 is positioned on the right, the b-side aperture part is driven into place. Further, it must be adaptability that the inspection may be effected way at a mid part of the pattern area with either of the a-side and b-side aperture parts inserted into place. With the confirmation effected, such as the above, concerning whether or not a pericle is provided, and further with the aperture 26, which restricts NA properly in response to the existence or nonexistence of the pericle, provided within the optical system, pattern evaluation with high accuracy is feasible over a wide area even in case the photo mask is fitted with a pericle.

Provision of such NA restricting aperture 26 as the above enables to effect the inspection of a pericle fitted photo mask in a state wherein the resolution characteristic of an originally furnished objective lens is not utilized fully. Namely, as the resolution (R) of a lens is expressed by R=kλ/NA (λ: a wavelength of the light applied for the inspection), provision of the aperture 26 results in lessening the capability of minute defect detection. Further, decreasing NA concurs with a fall of the luminous energy of light incident upon a sensor. These problems can be solved by using the aperture shown respectively in FIGS. 7A through 7D. Because the solution of such problems is based on the following considerations:

(1) If the pattern evaluation apparatus is capable of picking up a pattern defect signal with high sensitivity, it is unnecessary to focus a perfect image of the mask pattern on a sensor. Therefore, it is allowed that the NA stopping aperture is not of a conventional circular profile.

(2) The pericle frame is rectangular, likewise with a device pattern.

Figures 7A, 7B:
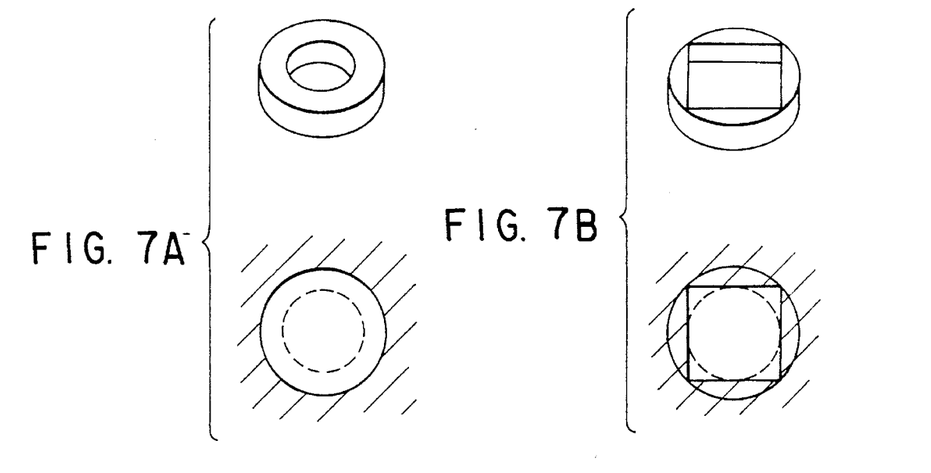
FIGS. 7A through 7D are respective views, each showing a profile of the NA aperture-stop.

FIGS. 7A through 7D are respective perspective views, each showing an NA stopping aperture and they also present respective plan views, each showing a region through which the light passes that goes through said aperture. FIG. 7A shows the profile of an aperture which is used for the case where the objective lens in said device is brought into use with the maximum NA selected. The broken line in the figure defines the aperture profile serviceable in case a pericle fitted photo mask is inspected.

Figure 8:
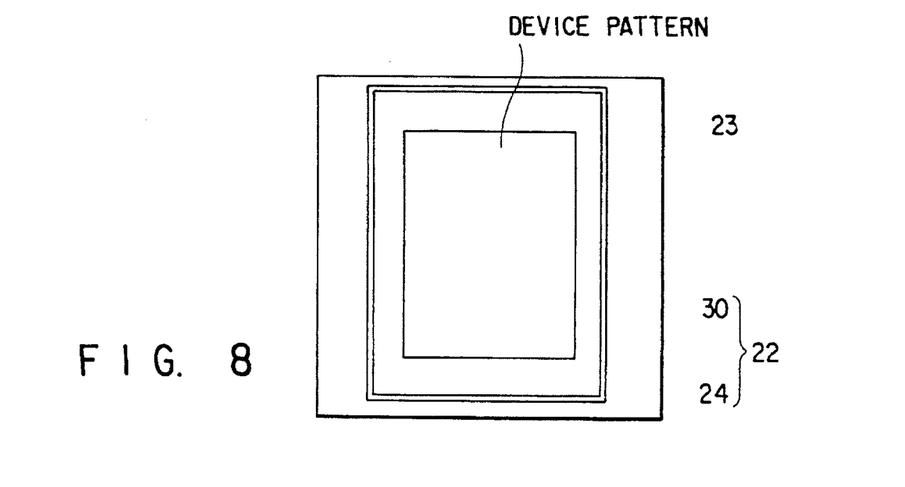
FIG. 8 is a plan view showing a pericle fitted photo mask.

As described above, both a pericle 30 and the pericle frame 24 are of a rectangular shape adapted to cover a device pattern area as shown in FIG. 8, giving raise no problem over use of an rectangular aperture as specified in FIG. 7B. It is understood that with the aperture applied of which profile is defined by the broken line in FIG. 7A, NA is stopped small in the whole directions while with the aperture given in FIG. 7B, NA viewed at an angle of 45° is kept available at the maximum at which the objective lens is used. In other words, use of a rectangular aperture enables the inspection with not only the sensitivity of detection not subjected to much fall but also the luminous energy of light incident upon a sensor not undergoing a decline.

Figure 7C:
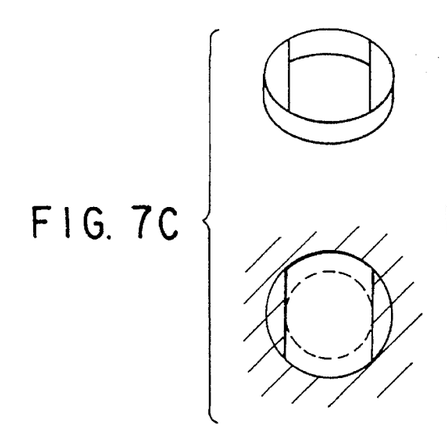
Figure 7D:
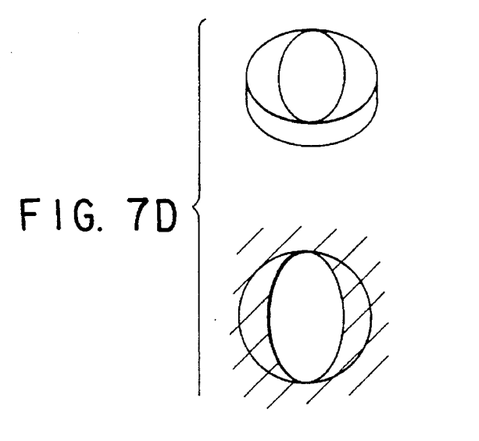

Further, the pericle frame is generally of a rectangular profile, and therefore, the pericle frame does not inflict the inspection area the interruption of a light beam along its longer side. Mostly, the inspection area of a shorter side raises a problem. Therefore, the aperture having an approximately oval profile as shown in FIG. 7C and another aperture of an elliptical form given in FIG. 7D are suited for use. Using the aperture of such a shape serves to further expand the area over which NA is kept available at the maximum at which the objective lens is brought into service, whereby the inspection is practicable with the sensitivity subjected to almost no decline and further with the luminous energy of light projected upon a sensor suffering no fall. Therefore, even where an aperture is provided within the optical system, depending on whether or not there is furnished a pericle, use of the aperture of the above-remarked profile enables to effect pattern evaluation with the fall in detection sensitivity and the decline of the luminous energy suppressed as much extent as possible.

Assuming that the distance from the pericle frame shown in FIG. 2 to the portion where the inspection is practicable is x and the pericle height is h, the size and profile of the aperture presented in FIGS.

FIGS. 7B through 7D are calculated such as those given by the following expression:

$$NA = \sin \theta = \sin (\tan^{-1} (x/h)) \quad (1)$$

In practicality, selecting such NA which is slightly larger than the NA calculated according to expression (1), namely the NA serving to improve the resolution characteristic gives rise to no problem. This is because in practical inspection, it does not take place that the pericle frame is positioned across the left and right edges of the objective lens at one time, but instead, the pericle frame approaches either of these lens edges, whereby no problem is confronted with even when the NA for the region opposite the pericle frame is selected sufficiently large.

Concretely, where the NA, which is calculated according to expression (1) in case there is provided a pericle under the condition that a lens with NA=0.8 is applied, is 0.55, an aperture corresponding to NA=approximately 0.65 is chosen for use.

Embodiment 2

Noticing the fact that even in case the pericle frame interrupts the beam of light, the luminous energy distribution is not affected, with nothing else declining than an overall fall of the luminous energy as given by a sensor output, the co-inventors will provide a pattern evaluating device, as a second embodiment of the present invention, which is capable of implementing high-precision pattern evaluation up to the adjacency of the pericle frame by changing the offset or the gain of a sensor signal while the inspection is progressing in the neighborhood of the pericle frame.

Namely, the co-inventors confirmed that pattern evaluation is made feasible with sufficient detecting sensitivity maintained unchanged even at the adjacency of the pericle frame only by uniformly changing the offsets or the gains of respective signals from the sensor applied for pattern inspection or merely by regularly changing the offset or the gain of each signal from the sensor, following not only the distance from the pericle frame to the point of inspection but also the propensity in a fluctuation of the luminous energy distribution.

Figure 9:
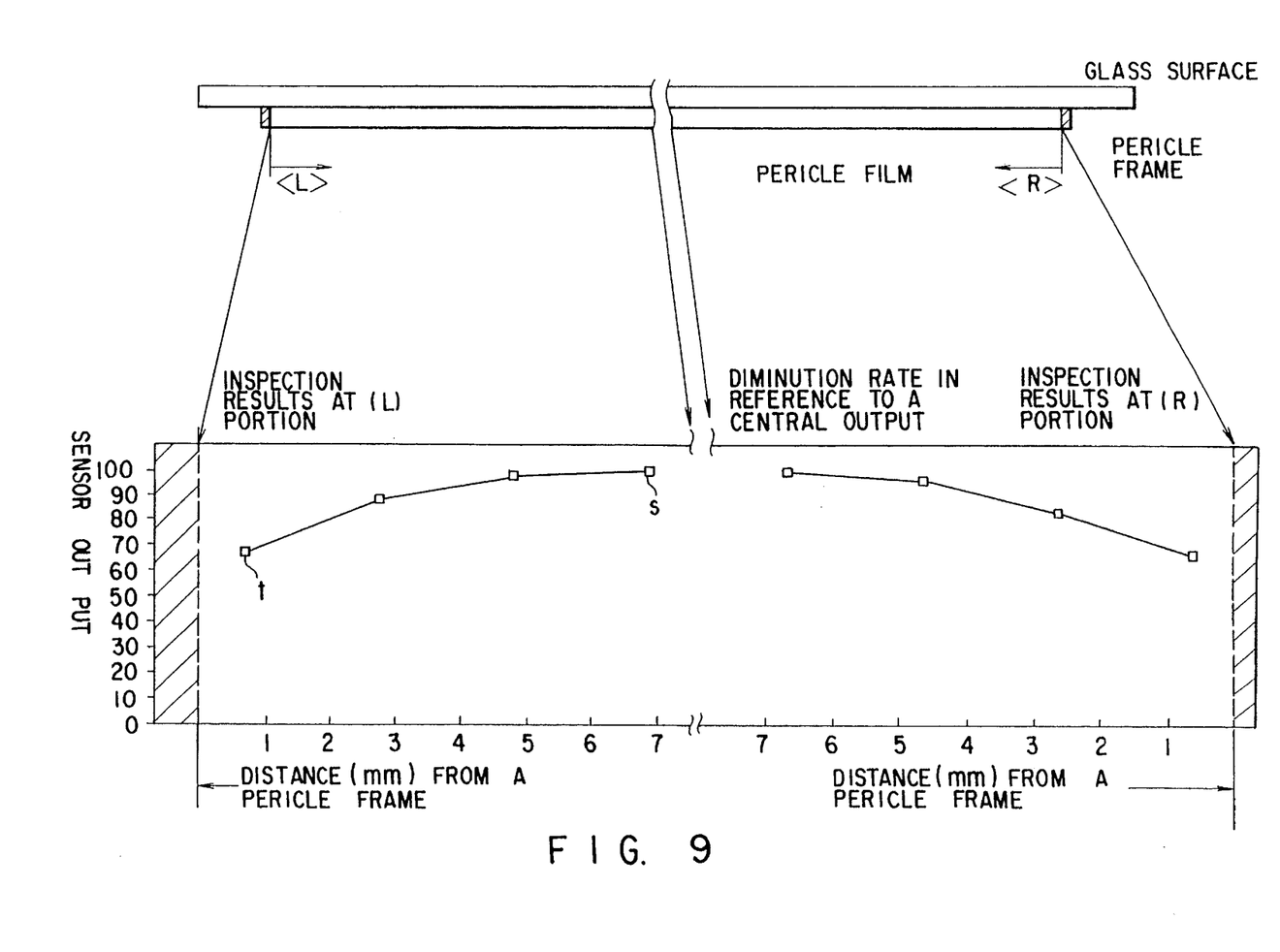
FIG. 9 presents the results of an experiment giving a fall of luminous energy due to the existence of a pericle.
Figure 10A:
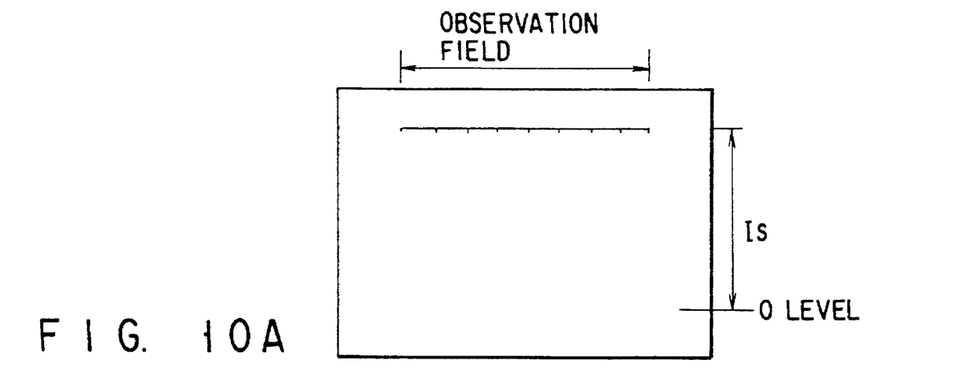
FIGS. 10A and 10B present the experimental results showing a change of the luminous energy distribution in the fall of luminous energy.
Figure 10B:
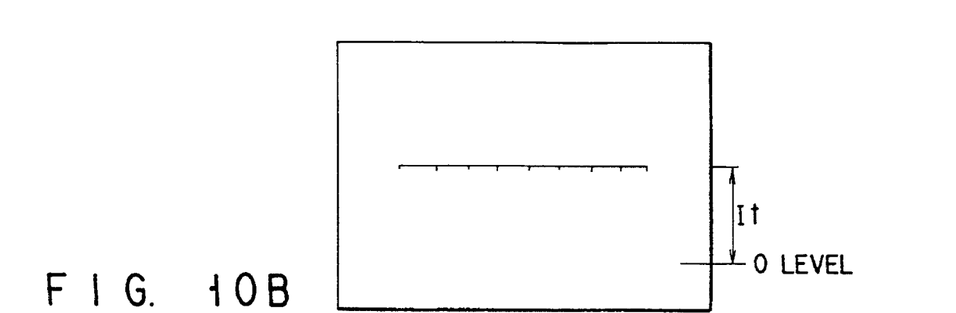

The consequences of the inquiry made, using the device shown in FIG. 4, after the relation between the distance from the pericle frame in FIG. 9 to a portion of inspection and a sensor output is presented hereunder. As is understood from FIG. 9, it is observed that in the neighborhood of the pericle frame, the sensor luminous energy gets falling. Presented in FIGS. 10A and 10B are the luminous energy distributions within the fields at respective points s and t in FIG. 9. As is clear from FIGS. 10A and 10B, a decline of the sensor luminous energy entails almost no change in the luminous energy distribution. This fact tells that by changing the sensor output gain corresponding to a fall of the luminous energy or the sensor output offset if required, high precision pattern evaluation is feasible even near the pericle frame.

A description is made concretely of the case where the interruption of a light beam by the pericle frame occurs, not affecting the luminous energy distribution, with an overall fall only of the luminous energy taking place as given by a sensor output. Further, a case where there occurs some change in the luminous energy distribution may be coped with, following the conception described hereunder.

Here, a method of changing the sensor output gain or offset in the inspection near the pericle frame when the luminous energy distribution is not affected as in the foregoing, is described. Further for simplicity of explanation, reference is made of the case where the sensor output gain only is changed. Presented in FIG. 11 are the inspection area (a region wherein there takes place no fall of the sensor's luminous energy and which is defined by a single-dot chain line) of a conventional pericle fitted photo mask and another inspection area (defined by a broken line) which the pattern evaluating device of the present invention can inspect.

Figure 11:
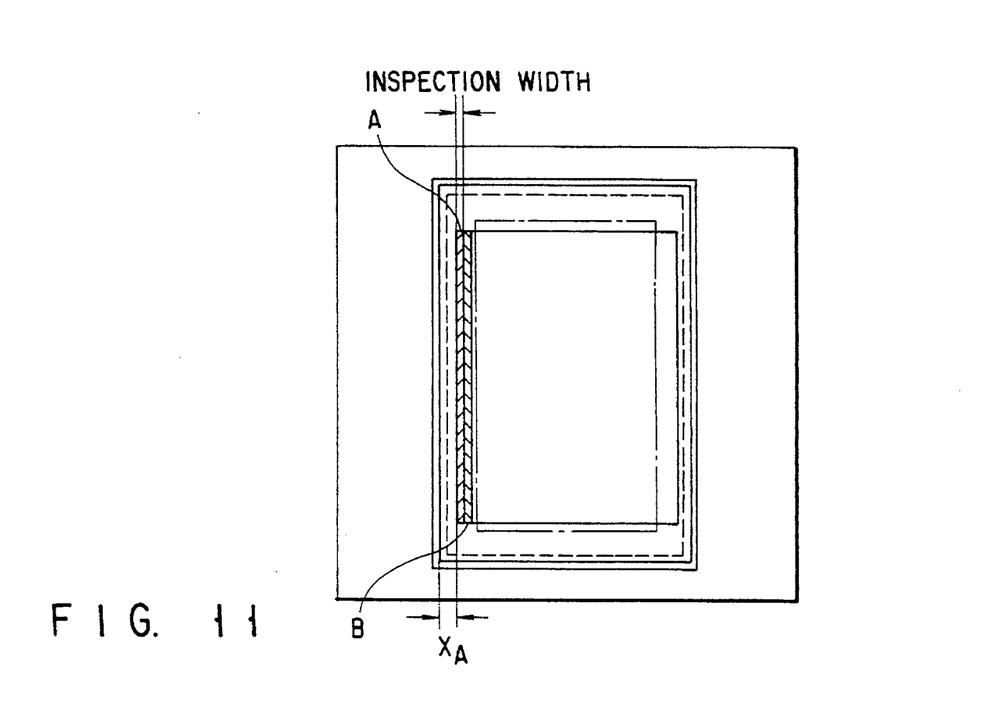
FIG. 11 is a view illustrating one example of a pattern evaluating method.
Figure 12:
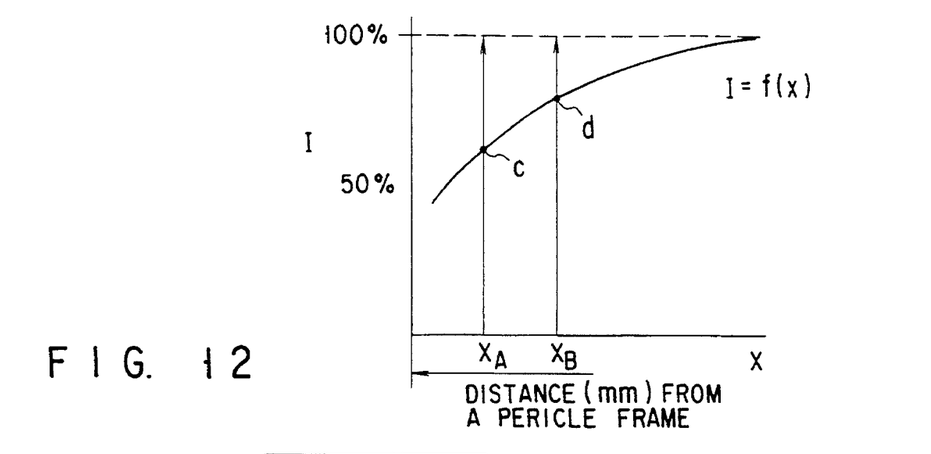
FIG. 12 is a view wherein the relation between the fall of luminous energy and the change of sensor gain.

Pattern defect inspection is carried out each over a narrow strip area (a shaded area) measuring an inspection width of approximately W=500 µm, as shown in FIG. 11. To start the inspection from point A in said figure, the luminous energy fall rate of light incident upon a sensor near the pericle frame is stored previously in memory means in a relation as shown in FIG. 12. With the distance from the pericle frame assumed as x for example and the function of a luminous energy decline likewise assumed as I=f(x), the relation therebetween is stored in advance. Or with the distance from the pericle frame is separately assumed, this distance and the experimental value of a luminous energy decline are stored in their mutual relation, whereby an actual luminous energy fall may be obtained via the compensation following the stored relation or otherwise calculated through a substitution with a new value. Basically, the rates of luminous energy decline on the left and right sides are symmetrical, whereby one function of a luminous energy decline in the neighborhood of the pericle frame may be expressed in I=f(x). Due to the optical characteristic, there may also take place a change of luminous energy. With this in view, it is conceivable to use another function of the fall of luminous energy in each lateral side of the pericle frame.

In doing the inspection over a barrow strip area shown in FIG. 11, if the bonding of a pericle is done parallel to the pattern involved, it may be said that the luminous energy over the area defined therebetween will almost constant. Therefore, sensor output gain $I_{100}/I_C$ is set so that the luminous energy at point c corresponding to distance $X_A$ from the pericle frame may be increased up to the broken line. Next when the inspection is effected at adjacent point B, sensor output gain $I_{100}/I_d$ is set again so that the luminous energy at point d corresponding to distance $X_B$ from the pericle frame, namely corresponding to a fall of the luminous energy at point B, which takes place while the table moves stepwise thereto may be raised up to the broken line. Distance $X_A$ is not up to the position of an inspection areal edge but may be defined as $X_A=X_A+W/2$. By repeating the procedure in the foregoing until such an area is reached where there occurs no fall of luminous energy, pattern evaluation with high accuracy may be effected continuously.

Figure 13:
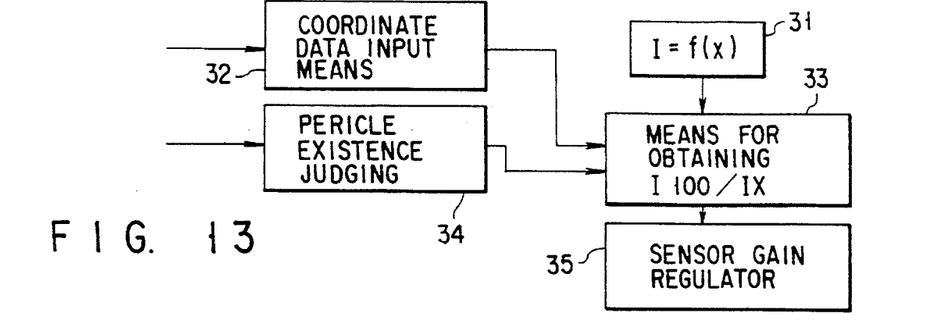
FIG. 13 is a block diagram illustrating a method of pattern evaluation according to the present invention.

For such a pattern evaluating device as the above, it is required that inspection coordinate (x, y) detecting means 32 (which applies the information from a position circuit 8 in FIG. 4), judging means 33 for deciding which of the gain setpoints is changed from a given inspection coordinates (x,y), and memory means 34 to store the information (this may be manually input by the operator at the time of inspection) as to whether or not a sample is provided with a pericle upon judgment thereof be provided in addition to memory means 31 for storing the rates of luminous energy decline, each of which is input to the sensor involved in the adjacency of the pericle frame, as shown in FIG. 13. The information from these means are input to a sensor output gain regulator 35.

Figure 14A:
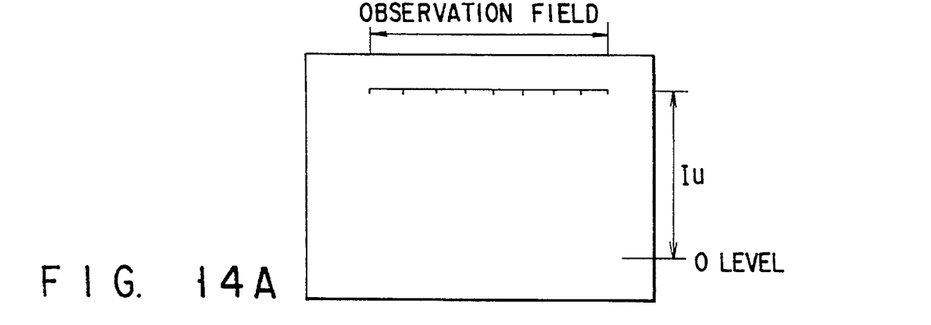
FIG. 14A is a view showing the luminous energy distribution within an observation field far remote from a pericle frame.
Figure 14B:
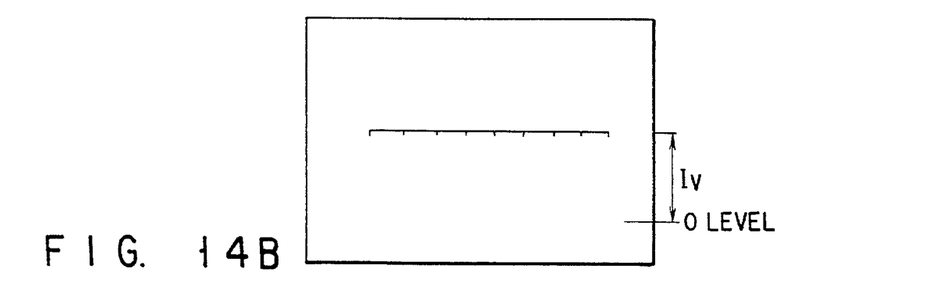
FIG. 14B is a view showing the luminous energy distribution within the observation field near the pericle frame.

Strictly, I=f(x) being a function of X, there occurs a change of luminous energy within an observation field. Further due to the resolution characteristic of the optical system, the luminous energy distribution may sometimes fluctuate within the observation field as specified respectively in FIGS. 14A and 14B. However, this fluctuation of the luminous energy is gradual and remains within a range of sufficient compensation. With a function defining this much of luminous energy distribution fluctuation provided, it becomes possible to compensate for each pixcel of the sensor.

As regards the present embodiment, how to compensate for measured pattern image data, concretely, how to make up or a sensor output gain or offset was described above. However, with the pattern evaluating device of a type wherein design data and measured data are compared with each other, image data which is considered to be available through measurement, is generated from design data. Therefore, it is believed that the engineers in such an industrial field may easily come to know by analogy how to generate image data from design data, but in the process of generating the image data which is expected to be available through measurement, design data may be such compensated for as remarked above. In other words, provision of said compensation which is made either for design data or measured pattern image data enables to inspect in the adjacency of the pericle frame.

Further, the position of a pericle (frame) fitted to the photo mask concerned is generally found with a deflection of approximately ±0.5 mm. Thus, it is necessary to detect the pericle (frame) position to undertake high-precision pattern evaluation. With this in mind, it is accordingly preferred that means of measuring the pericle (frame) position be provided. In such a case, the installation of a position detecting sensor for exclusive use with the pericle (frame) results in raising the device cost. As means of detecting said pericle (frame) position, there is quoted means for not only driving a slide table in each of x and y directions but also deciding the pericle (frame) position on the basis of a luminous energy changing rate depending on the sensor output, and calculating the relation between the pattern to go through the inspection and the pericle frame. When this means is selected, it is essential that a photo mask pattern be made of such a material with some transparency. Therefore, depending on the kinds of material selected to prepare a photo mask pattern, due instrumentation may sometimes be rendered impracticable.

As other means to detect the pericle (frame) position, there is cited means to measure the output of an auto-focusing sensor for use in precision-focusing the objective lens and the photo mask and to detect the pericle (frame) position. With this means, the output of the auto-focusing sensor is free from pattern dependability, giving raise to no such problem as that with which said means in the foregoing is confronted. Further, in the case with this means, when the detecting position approaches the pericle frame, the beam of light from the auto-focusing sensor is interrupted, causing a change or an error of luminous energy. However, the problems in these regards are nullified by reading the slide table position through the position circuit. As means for detecting said pericle (frame) position, various means are conceivable, which drive the table, whereby to decide the pericle (frame) position by relating some change of the signal involved with the table position.

In the pattern evaluating device including those means, it is allowed that a portion which is affected by a fall of the luminous energy of light projected upon the sensor in the neighborhood of the pericle frame, and a portion which is relatively remote from the pericle frame, thereby confronting with no problem over a decline of luminous energy, are separated from one another for separate inspection or irrespective of said portion which is affected by a fall of the luminous energy of light incident upon the sensor in the neighborhood of the pericle frame and said portion which is relatively remote from the pericle frame, thereby confronting with no problem over a decline of luminous energy, the sensor amplifier output gain or offset is changed, whereby serial inspection may be implemented.

As described above, the pattern evaluation apparatus of the present invention comprises light focusing means to converge the rays of light from a light source upon a sample with a pattern formed thereon, an objective lens set behind said sample and through which the light having penetrated through said sample passes, an aperture member provided behind said objective lens and stopping the diameter of a light beam which has penetrated through said objective lens, a photo receiving element installed behind said aperture member and receiving the light which has had the diameter of a light beam stopped by said aperture member, and judging means to evaluate said pattern, following the information of the light received by said photo receiving element and which corresponds to said pattern, wherein said aperture member is characterized by the practicability to change the numerical aperture according to whether or not said sample is provided with a pericle, whereby NA may be rendered variable at the time of pattern evaluation and further, high-precision pattern evaluation may be feasible.

Further, the pattern evaluating device of the present invention comprises light focusing means to converge the rays of light from a light source upon a sample with a pattern formed thereon, an objective lens set behind said sample and through which the light having penetrated through said sample passes, a photo receiving element installed behind said objective lens and receiving the light which has passed through said objective lens, and judging means to evaluate said pattern, following the information of the light received by said photo receiving element and which corresponds to said pattern, wherein said sample is provided with a pericle, and said judging means is characterized in that it evaluates said pattern, according to the information obtained via arithmetic processing of the information of the light corresponding to said pattern, when the inspection is effected near the edge of said pericle, whereby high-precision pattern evaluation is practicable up to the adjacency of the pericle frame.

Further, the method of pattern evaluation according to the present invention enables high-precision pattern evaluation even in the neighborhood of the pericle frame within the pattern area available with a pericle fitted photo mask applied.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A pattern evaluating device comprising:

light irradiating means for irradiating the rays of light from a light source upon an object carrying a pattern;

an objective lens through which the light having penetrated through said object passes;

an aperture member stopping the diameter of a light beam which has passed through said objective lens;

a photo receiving element receiving the light beam which has had the diameter stopped by said aperture member; and judging means for evaluating said pattern, following the information received by said photo receiving element and which corresponds to said pattern; and wherein said aperture member is capable of changing a numerical aperture according to whether or not said object is provided with a pericle.

2. The apparatus according to claim 1, further comprising luminous energy adjusting means for adjusting the luminous energy along with a change of said numerical aperture so that the luminous energy of light incident upon said photo receiving element may be approximately constant.

3. The apparatus according to claim 2, wherein said aperture member and said luminous energy adjusting means are actuated, following the information concerned with whether or not there is provided a pericle and which an operator has input or via computer control according to a signal of detecting whether or not a pericle is provided.

4. The apparatus according to claim 1, wherein the aperture profile of an aperture member for setting the numerical aperture on the side of an object is approximately rectangular.

5. The apparatus according claim 1, wherein said aperture member is incorporated in said apparatus regardless of whether or not a pericle is provided.

6. The apparatus according to claim 1, wherein the straight line portions of an aperture of said aperture member are parallel respectively to the straight line portions of said pericle frame.

7. The apparatus according to claim 1, wherein the NA on the side of an object and which is limited by said aperture member, is somewhat larger than theoretical NA (=sin $(\tan^{-1}(x/h))$) calculated with the pericle height and the distance from the pericle frame to the portion where the inspection is impracticable, assumed as h and x, respectively.

8. A pattern evaluating device comprising:

light irradiating means for irradiating the rays of light from a light source upon an object;

an objective lens through which the light having penetrated through said object passes;

a photo receiving element receiving the light which has passed through said objective lens; and judging means for evaluating said pattern, following the information of the light received by said photo receiving element and which corresponds to said pattern; and wherein said object is provided with a pericle, and said judging means evaluates said pattern, following the information obtained via arithmetic processing of the information of the light corresponding to said pattern, when the inspection is effected near the edge portion of said pericle.

9. The apparatus according to claim 8, further comprising memory means for storing the rates of a luminous energy fall of the light which is projected, near said pericle frame, being incident upon a sensor frame.

10. The apparatus according to claim 8, further comprising means for not only judging whether or not an object is provided with a pericle but also storing the information of judgment.

11. The apparatus according to claim 8, further comprising means for pericle position detecting.

12. The apparatus according to claim 11, wherein the means for pericle position detecting is means for deciding the position of a pericle, following the luminous energy change rate given by a sensor output with a slide table moved in each of x and y directions.

13. The apparatus according to claim 11, wherein the means for pericle position detecting is means for deciding the position of a pericle, following the change of an autofocusing sensor output with the slide table moved in each of x and y directions.

* * * * *